US008895074B2

(12) United States Patent     (10) Patent No.:    US 8,895,074 B2
Driscoll     (45) Date of Patent:    Nov. 25, 2014

(54) THERAPEUTIC APPLICATION OF PARENTERAL KRILL OIL

(75) Inventor: David F. Driscoll, Bridgewater, MA (US)

(73) Assignee: Stable Solutions LLC, Goleta, CA (US)

( * ) Notice: Subject to any disclaimer, the term of this patent is extended or adjusted under 35 U.S.C. 154(b) by 0 days.

(21) Appl. No.: 13/161,101

(22) Filed: Jun. 15, 2011

(65) Prior Publication Data

US 2012/0321720 A1    Dec. 20, 2012

(51) Int. Cl.

| | | |
|---|---|---|
| A61K 35/12 | (2006.01) | |
| A61K 35/60 | (2006.01) | |
| C11B 1/00 | (2006.01) | |
| A61K 31/612 | (2006.01) | |
| A61K 9/00 | (2006.01) | |
| A61K 45/06 | (2006.01) | |
| A61K 31/6615 | (2006.01) | |
| A61K 31/23 | (2006.01) | |
| A61K 9/107 | (2006.01) | |
| A61K 35/56 | (2006.01) | |

(52) U.S. Cl.
CPC ............ *A61K 31/6615* (2013.01); *A61K 31/612* (2013.01); *A61K 9/0019* (2013.01); *A61K 45/06* (2013.01); *A61K 31/23* (2013.01); *A61K 9/107* (2013.01); *A61K 35/612* (2013.01)
USPC ................................ 424/522; 424/523; 554/8

(58) Field of Classification Search
USPC ....................................... 424/522, 523; 554/8
See application file for complete search history.

(56) References Cited

U.S. PATENT DOCUMENTS

| | | | |
|---|---|---|---|
| 5,434,183 A | 7/1995 | Larsson-Backstrom | |
| 2006/0078625 A1* | 4/2006 | Rockway | 424/538 |
| 2008/0274203 A1 | 11/2008 | Bruheim et al. | |
| 2009/0099261 A1* | 4/2009 | Bell et al. | 514/560 |
| 2010/0062057 A1* | 3/2010 | Berge et al. | 424/455 |
| 2010/0130619 A1* | 5/2010 | Schwarz et al. | 514/690 |

FOREIGN PATENT DOCUMENTS

| | | |
|---|---|---|
| EP | 2 153 736 A1 | 2/2010 |
| JP | 8-231391 A | 9/1996 |
| WO | WO 0202394 A2 * | 12/2002 |
| WO | WO 2008/117062 A1 | 10/2008 |

OTHER PUBLICATIONS

Goldfarb RD et al, Protein-free Phospholipid Emulsion Treatment Improved Cardiopulmonary Function and Survival in Porcine Sepsis, Am J Physiol Regul Integr Comp Physiol 284: R550-R557, 2003.*
Mori TA et al, Effect of Eicosapentaenoic Acid and Docosahexaenoic Acid on Oxidative Stress and Inflammatory Markers in Treated-Hypertensive Type 2 Diabetic Subjects, Free Radic Biol Med 35: 772-781, 2003.*
Cave G et al, Intravenous Lipid Emulsion as Antidote Beyond Local Anesthetic Toxicity: A Systematic Review, Acad Emerg Med 16: 815-825, 2009.*
De Meijer et al., "Fish Oil-Based Lipid Emulsions Prevent and Reverse Parenteral Nutrition-Associated Liver Disease: The Boston Experience" Journal of Parenteral and Enteral Nutrition, (Sep./Oct. 2009), vol. 33, No. 5, pp. 541-547, Sage, The American Society for Parenteral & Enteral Nutrition, http://pen.sagepub.com/content/33/5/541.
Dellinger et al., "Efficacy and Safety of a Phospholipid Emulsion (GR270773) in Gram-Negative Severe Sepsis: Results of a Phase II Multicenter, Randomized, Placebo-Controlled, Dose-Finding Clinical Trial" Critical Care Medicine, (2009), vol. 37, No. 11, pp. 2929-2938.
Driscoll et al., "Lipid Emulsions in Parenteral Nutrition" In Parenteral Nutrition. Rombeau J.L., Rolandelli R. (eds): W. B. Saunders Company, Philadelphia, PA, (2001), pp. 35-59.
Driscoll et al., "Pharmacopeial Compliance of fish Oil-Containing Parenteral Lipid Emulsion Mixtures: Globule Size Distribution (GSD) and Fatty Acid Analyses" International Journal of Pharmaceutics, (Sep. 8, 2009), vol. 379, Issue 1, pp. 125-130.
Gordon et al., "Neutralization of Endotoxin by a Phospholipid Emulsion in Healthy Volunteers" Journal of Infectious Diseases, (May 1, 2005), vol. 191, Issue 9, pp. 1515-1522.
Hiller et al., "Safety of High Volume Lipid Emulsion Infusion" Regional Anesthesia and Pain Medicine, (Mar.-Apr. 2010), vol. 35, No. 2, pp. 140-144.
Jones et al., "Toxicity Testing of Fat Emulsions for Intravenous Administration" American Journal of Clinical Nutrition, (Jan. 1965), vol. 16, No. 1, pp. 62-67.
Larsen et al., "Propofol in a Formulation (Propofol MCT/LCT): Effect on Injection Pain in Children" A Comparison with Propofol-LCT, Anaesthesist, (Sep. 2001), vol. 50, No. 9, pp. 676-678.
Le et al., "Parenteral Fish Oil as Monotherapy Improves Lipid Profiles in Children with Parenteral Nutrition-Associated Liver Disease" Journal of Parenteral and Enteral Nutrition, (Sep. 2010), vol. 34, No. 5, pp. 477-484, Sage, The American Society for Parenteral & Enteral Nutrition, http://pen.sagepub.com/content/34/5/477.
Lee et al., "Saturated, but not n-6 Polyunsaturated, Fatty Acids Induce Insulin Resistance: Role of Intramuscular Accumulation of Lipid Metabolites" Journal of Applied Physiology, (May 2006), vol. 100, No. 5, pp. 1467-1474.
Rangel-Frausto et al., "The Natural History of the Systemic Inflammatory Response Syndrome (SIRS): A Prospective Study" Journal of the American Medical Association (JAMA), (Jan. 11, 1995), vol. 273, No. 2, pp. 117-123.
Turner-Lawrence et al., "Intravenous Fat Emulsion: A Potential Novel Antidote" Journal of Medical Toxicology, (Jun. 2008), vol. 4, No. 2, pp. 109-114.

(Continued)

*Primary Examiner* — Susan Hanley
*Assistant Examiner* — Paul Martin
(74) *Attorney, Agent, or Firm* — Buchanan Ingersoll & Rooney PC

(57) ABSTRACT

A method of parenterally administering a composition, the method including parenterally administering to a person a composition including krill oil in an oil-in-water emulsion. A parenterally applicable pharmaceutical composition, including an oil-in-water emulsion including a phospholipid obtained from a marine crustacean.

35 Claims, No Drawings

(56) References Cited

OTHER PUBLICATIONS

Winther et al., "Elucidation of Phosphatidylcholine Composition in Krill Oil Extracted from *Euphausia superba*" Lipids, (Jan. 2011), vol. 46, No. 1, pp. 25-36, published online Sep. 17, 2010.

Larsen et al., "Less Pain on Injection by a new Formulation of Propofol? A Comparison with Propofol LCT" Anaesthesist, (Nov. 2001), vol. 50, No. 11, pp. 842-845, (Abstract only).

Extended Search Report issued by the European Patent Office issued in corresponding European Patent Application No. 11179821.1 dated Jan. 23, 2012 (7 pages).

Database WPI, Week 199806, Thomson Scientific, London, GB; AN 1998-056091, XP002666694, JP 8231391, Sep. 10, 1996 (abstract).

Driscoll, David F., et al., "The influence of medium-chain triglycerides on the stability of all-in-one formulations," *International Journal of Pharmaceutics*, 2002, pp. 1-10, 240, Elsevier Science B.V. The Netherlands.

Bistrian, Bruce R., "Clinical Aspects of Essential Fatty Acid Metabolism; Jonathan Rhoads Lecture," *Journal of Parenteral and Enteral Nutrition*, 2003, pp. 168-175, vol. 27, No. 3, Sage, The American Society for Parenteral & Enteral Nutrition, http://pen.sagepub.com/content/27/3/168.

"*Omega-3-Acid Triglycerides: Omega-3 Acidorum Triglycerida*," European Pharmacopoeia 5.4, Jan. 2005:1352 corrected, 2005, Monograph 1352, pp. 3995-3997.

Larsen et al., "Propofol in a New Formulation (Propofol MCT/LCT): Effect on Injection Pain in Children, A Comparison with Propofol-LCT," Anaesthesist, (Sep. 2001), vol. 50, No. 9, pp. 676-678, with partial English translation.

Larsen et al., "Less Pain on Injection by a New Formulation of Propofol? A Comparison With Propofol-LCT," Anaesthesist, (Nov. 2001), vol. 50, No. 11, pp. 842-845, with partial English translation.

International Search Report (PCT/ISA/210) mailed on Jul. 26, 2012, by the European Patent Office as the International Searching Authority for International Application No. PCT/IB2012/001156.

* cited by examiner

THERAPEUTIC APPLICATION OF PARENTERAL KRILL OIL

BACKGROUND

Krill oil is a unique marine oil containing omega-3 or n-3 fatty acids (FAs), wherein the bioactive eicosapentaenoic acid (EPA) and docosahexaenoic acid (DHA) are present (i.e., comprising up to 35%$_{w/w}$, of the FA profile) mainly in phospholipids or PLs (up to 95%$_{w/w}$), and containing up to 60% PLs and up to 45% triglycerides in the oil.[1] In contrast, current sources of n3-FAs in commercial parenteral or injectable lipid emulsions consist of approximately 30 to 60%$_{w/w}$ concentration, but are nearly entirely contained in fish oil triglycerides (TG). Of note, the European Pharmacopeia (Pharm Eur) has two official monographs for n3-FAs derived from fish oil triglycerides. The first monograph was adopted in 1999 and includes the following title, monograph number and specifications:

1. Omega-3 Acid Triglycerides, Pharm Eur Monograph 1352 (Omega-3 acidorum triglyceride)
   Content:
   Sum of the contents of the omega-3 acids EPA and DHA, expressed as triglycerides: minimum 45.0 percent; total omega-3 acids, expressed as triglycerides: minimum 60.0 percent.

In 2005, a second Pharm Eur monograph was adopted and includes the following title, monograph number and specifications:

2. Fish Oil, Rich in Omega-3 Acids, Pharm Eur Monograph 1912 (Piscis oleum omega-3 acidis abundans)
   Content:
   EPA, expressed as triglycerides: minimum 13.0 percent, DHA, expressed as triglycerides: minimum: 9.0 percent, total omega-3 acids, expressed as triglycerides: minimum 28.0 percent.

Of the two monographs, only Pharm Eur Monograph 1352 is specifically indicated for parenteral use.[2] However, depending upon the manufacturer, two commercially available parenteral emulsions employ the pharmacopeial standards of either Monograph 1352 or 1912, i.e., one brand of fish oil-containing injectable emulsion contains approximately one-half the concentration of the bioactive omega-3 fatty acids, EPA and DHA vs. another brand of fish oil-containing emulsion, and hence they are not bioequivalent.[3] Ideally, it may be beneficial to employ the specifications of Pharm Eur Monograph 1352, a greatly purified fish oil triglyceride source of n3-FAs, especially when administered by the intravenous route of administration.

Omega-3 fatty acids are classified as highly polyunsaturated fatty acids (PUFA), containing multiple double bonds that are extremely susceptible to oxidative degradation. Unsaturated fatty acids have specific nomenclature involving 3 general terms: 1) number of carbons; 2) number of double bonds; and, 3) the carbon containing the first double bond. There are 3 main families of unsaturated fatty acids important in human metabolism and they include the omega-3's (e.g., EPA containing 20 carbons, 5 double bonds beginning on the 3$^{rd}$ carbon from the methyl end of the hydrocarbon chain, denoted as 20:5n3); the omega-6's (e.g., arachidonic acid, or AA, containing 20 carbons, 4 double bonds beginning on the 6$^{th}$ carbon, denoted as 20:4n6); and finally, the omega-9's (e.g., oleic acid containing 18 carbons, 1 double bond beginning on the 9$^{th}$ carbon, denoted as 18:1n9). They are classified as highly polyunsaturated, polyunsaturated, and monounsaturated fatty acids, respectively. Oxidation of highly PUFAs, such as EPA (20:5n3) and DHA (22:6n3), not only degrades their important clinical bioactivities (such as therapeutic decreases in: inflammation, oxidative stress, immunosuppression and ischemia), but also produces volatile degradation products known as reactive oxygen species, that may have clinically relevant and harmful side effects to vital organs (e.g., heart, brain, lungs, liver and kidneys), especially in critically ill patients during acute metabolic stress (i.e., the systemic inflammatory response syndrome). Therefore, minimizing the oxidation of vegetable- or marine-based polyunsaturated fatty acids in injectable lipid emulsions is desirable. This can be achieved based on the location of the polyunsaturated fatty acid on the glyceride backbone, with position-2 being most preferable in this regard (as well as with respect to bioavailability). Alternatively, antioxidants, such as alpha tocopherol, are either naturally present in small amounts (e.g., alpha-tocopherol in soybean oil, ~20 mg/L) or are added to the lipid injectable emulsion formulation in amounts approximating 200 mg/L. Alpha-tocopherol is an example of a parenteral antioxidant that protects these bioactive fatty acids from chemical breakdown and subsequent potential clinical harm, and it is recognized as a suitable parenteral pharmaceutical adjuvant by both the European and the United States Pharmacopeias (USP). On the other hand, in addition to its high PL contents, krill oil possesses another unique attribute, in that it contains the naturally occurring antioxidant, astaxanthin, but in amounts 10× to 100× higher than the antioxidants naturally found in commonly used polyunsaturated triglyceride oil-in-water parenteral emulsions.[1] Astaxanthin is not approved for use in humans as a parenteral surfactant.

Despite this benefit, the uniquely high PL content of krill oil (e.g., in its current composition[1]) may render it unsuitable as a major source of n-3 FAs in lipid injectable emulsions. Current parenteral dispersions contain egg phospholipids as a surfactant to stabilize various triglyceride oil-in-water (o/w) emulsions. Like egg phospholipids, phosphatidyl choline is a major phosphatide in krill oil phospholipids.[4] The proportion of phospholipids to triglycerides (PL:TG ratio) in injectable lipid emulsion formulations should be no greater than 0.06. For example, a standard 20% soybean oil-in-water injectable lipid emulsion contains 12 g/L of PL and 200 g/L of triglycerides. Higher PL:TG ratios (i.e., 0.12, e.g., 10% oil-in-water emulsions with 12 g/L of egg PL) have been shown to interfere with lipoprotein lipase and impair plasma clearance of infused triglycerides (i.e., hypertriglyceridemia) in acutely ill infants, and in adults at high infusion rates.[5] Therefore, using krill oil in its present form as the principal lipid source in injectable emulsions does not seem to be clinically acceptable.

Another high concentration parenteral phospholipid-based injectable emulsion (92.5% phosphatidyl choline/7.5% triglyceride) has been given in an attempt to neutralize the clinical sequelae from bacterial endotoxin.[6] Although some benefits were observed, the primary study endpoint, a nonparametric "clinical scoring system" based on various symptoms (chills, headaches, myalgias, nausea and headaches), was applied and analyzed by parametric statistical methods (i.e., a 2-tailed t-test). However, this significant design flaw negated the purported benefits of the study. A follow-up randomized clinical trial involving 235 medical centers worldwide showed no significant benefit on 28-day all-cause mortality, nor was there a reduction in the onset of new organ failure.[7] Moreover, the high-dose arm of the study had to be stopped due to an increase in life-threatening adverse events. It is possible, as with effective parenteral surfactants, that a mixture of phosphatides is more efficacious as a pharmaceutical aid, and that a similar composition may be needed for clinical safety and efficacy in this patient population.

SUMMARY

According to an exemplary embodiment, a method of parenterally administering a composition is provided, the method comprising parenterally administering to a person a composition comprising krill oil in an oil-in-water emulsion.

According to another exemplary embodiment, a parenterally applicable pharmaceutical composition is provided, comprising an oil-in-water emulsion comprising a phospholipid obtained from a marine crustacean.

DETAILED DESCRIPTION

According to an exemplary aspect, provided is a composition having an omega-3 fatty acid-containing phospholipid obtained from, for example, a marine crustacean such as krill. The use of exemplary compositions in various applications, for example, as a surfactant, as a therapy for endotoxicosis in sepsis, and/or as an antidote for lipophilic drugs, can result in improvements in the safety and efficacy over existing therapies. Such composition can be administered parenterally. According to an exemplary aspect, therapeutic indications of a marine oil obtained from a crustacean, for example, krill oil, in parenteral dosage forms for treatment of several clinical conditions are provided.

The composition can contain an oil obtained from a marine crustacean such as, for example, krill (Euphausiacea). As used herein, the term "krill oil" can include an oil directly obtained from krill, an oil which is derived from a krill source and which has been further modified/processed, and combinations thereof.

The krill oil contains phospholipids to which omega-3 fatty acids are attached. For example, the krill oil can contain omega-3 fatty acid-containing phospholipids in an amount of about 20 to about 60%, for example, from about 30 to about 50%, based on the weight of the krill oil. In an exemplary embodiment, the krill oil can contain omega-3 fatty acid-containing triglycerides in an amount of less than about 30%, for example, less than about 5%, based on the weight of the krill oil. In an exemplary embodiment, the krill oil can be substantially free of omega-3 fatty acid-containing triglycerides. For example, both phospholipids (PLs) and triglycerides (TGs) possess a 3-carbon backbone (triacylglycerol) where certain functional groups attach to each of the carbons, with positions-1, -2, and -3 noted as sn1, sn2 and sn3, respectively. The sn1 and sn2 positions in both PLs and TGs can contain long-chain fatty acids, such as 18-carbon compounds (e.g., linoleic, alpha-linolenic, oleic and stearic acids) and/or very-long chain fatty acids containing 20 or more carbons (e.g., arachidonic, eicospentaenoic, docsapentaenoic and docosahexaenoic acids). In TGs, the sn3 position is also occupied by the above long-chain fatty acids, and as such these compounds are known as "neutral fat", whereas in PLs the sn3 position is occupied by phosphoric acid bound to an alcohol such as choline, ethanolamine, serine, inositol, etc., that significantly alters the molecule, conferring to it both hydrophilic and hydrophobic properties, known as an amphiphilic compound. As part of the structural make-up of biological membranes, and possessing amphiphilic properties, PLs serve a vital role in many metabolic processes.

In an exemplary embodiment, a pre-determined amount of the omega-3 fatty acid-containing phospholipids contain omega-3 fatty acids attached to the first and second positions of the phospholipid, but not the third position of the phospholipid. That is, a predetermined amount of the omega-3 fatty acid-containing phospholipids can contain an omega-3 fatty acid in the second position (i.e., the middle position) of the phospholipid. For example, the omega-3 fatty acid-containing phospholipids containing omega-3 fatty acids attached to the first and second positions of the phospholipid, but not the third position of the phospholipid, can be present in an amount of about 70% to about 80%, for example, from about 80% to about 95%, based on the total weight of the omega-3 fatty acid-containing phospholipids.

In an exemplary embodiment, the marine crustacean or krill oil can be distinguishable from fish oils at least based on (1) the phospholipid contents, (2) the content of omega-3 fatty acid-containing phospholipids, (3) the content of omega-3 fatty acid-containing triglycerides, and/or (4) the content of the omega-3 fatty acid-containing phospholipids which contain omega-3 fatty acids attached to the first and second positions of the phospholipid, but not the third position of the phospholipid. For example, the marine crustacean or krill oil can contain a higher concentration of omega-3 fatty acid-containing phospholipids, a lower concentration of omega-3 fatty acid-containing triglycerides, and/or a higher content of the omega-3 fatty acid-containing phospholipids which contain omega-3 fatty acids attached to the first and second positions of the phospholipid, but not the third position of the phospholipid.

The amount of the krill oil in the composition can depend, for example, on the specific application of the composition. For example, the krill oil can be present in an amount of from about 1% to about 20%, for example, from about 5% to about 10%, based on the total weight of the composition.

The ratio of oil to water in the oil-and-water emulsion can depend, for example, on the specific application of the composition. For example, the weight ratio of oil to water in the composition can range from about 1:99 to about 20:80, for example, from about 5:95 to about 10:90.

The composition can contain additional components, and the presence and amounts of the additional components can depend, for example, on the specific application of the composition. Exemplary examples of emulsion compositions are set forth in Table 1. For example, the composition can include a fish oil, MCT oil, and/or egg phospholipids. For example, the composition can include a total fish oil content of from about 0% to about 18%, for example, from about 5% to about 10%, based on the weight of the composition. The fish oil can include n3-FA-containing triglycerides. For example, the composition can include a total MCT oil content of from about 0% to about 10%, for example, from about 4% to about 8%, based on the weight of the composition. For example, the composition can include a total egg phospholipid content of from about 0% to about 1.8%, for example, from about 0.6% to about 1.2%, based on the weight of the composition. For example, the composition may contain astaxanthin of from about 0.0012% to about 0.02%, for example, from about 0.04% to 0.25%, based on the weight of the composition. Exemplary fish oils, MCT oils and egg phospholipids and contents thereof are disclosed in U.S. application Ser. No. 12/382,196 filed on Mar. 11, 2009, and International Application No. PCT/US2010/000723 filed Mar. 11, 2010, the entire contents of which are incorporated by reference herein.

For example, the krill oil can be used as an additive in an omega-3 enriched fish oil-in-water parenteral nutrition emulsion. The krill oil can be used in conjunction with the compositions and/or methods disclosed in International Application No. PCT/US2010/000723 filed on Mar. 11, 2010; U.S. application Ser. No. 12/382,196 filed on Mar. 11, 2009; and/ or U.S. application Ser. No. 12/923,257 filed on Sep. 10, 2010, the entire contents of which are incorporated by reference herein.

The krill oil can be subjected to various processing steps, and the specific processing steps employed can depend on, for example, the desired characteristics of the oil. For example, modifications or purifying steps are possible, and may be desirable in order to optimize the clinical utility of this unique source of n3-FAs. These changes, for example, may include deliberate alterations in the fatty acid profiles of the krill oil, such as 1) increasing the concentrations of the bioactive n3-FAs, EPA and DHA (e.g., from up to 35% w/w to 45% w/w); 2) changing the distribution of these bioactive omega-3 fatty acid levels in the phospholipids fraction or the triglyceride (TG) fraction of the oil (e.g., ↑PL ↓TG, ↓PL ↑TG, PL=TG); 3) maximizing the probability of locating the n3-FAs in the 2-position of the phospholipids (to optimize incorporation into biological membranes, and enhance stability); 4) reducing the concentration of potentially clinically deleterious saturated fatty acids[8] present (e.g., myristic acid, 14:0 and palmitic acid, 16:0); 5) reducing the concentration of free fatty acids; 6) minimizing the presence of lysophosphatidyl choline; 7) modifying the effective concentrations of astaxanthin, as well as any other pharmaceutical modifications to render the krill oil safe for intravenous administration. Table 2 provides examples of modifications of fatty acids and lipids from current krill oil compositions.[1] that might be designed by applying appropriate physical and chemical methods to form specialized compositions in order to achieve certain clinical applications. The examples are in no way meant to be limiting but to illustrate the possibilities recognizing there are numerous permutations and combinations possible. The high concentration of PLs in krill oil is unique among marine oil sources, and the possible modification of the natural source can exploit this aspect, for example, with respect to manipulating the composition to enhance the clinical (likelihood of structuring a stereospecific preponderance for the signaling n3-FAs, i.e., EPA and DHA, in the 2-position of the PLs present) and pharmaceutical (safe and efficacious parenteral marine oil) attributes.

According to an exemplary aspect, a method of parenterally administering a composition is provided, the method comprising parenterally administering to a person a composition containing krill oil in a parenteral oil-in-water emulsion as an alternative surfactant to egg lecithin or in combination with egg lecithin to improve the physical stability of the emulsion (Table 3). Achieving the physical stability of an injectable emulsion is defined as maintaining a homogenous distribution of submicron droplets, and minimizing the population of large-diameter (>1 micrometer) fat globules. During instability, the population of large-diameter fat globules grow (via coalescence or fusion of submicron lipid droplets), increasing the danger (e.g., pulmonary embolism, hypertriglyceridemia, liver dysfunction) from the injectable emulsion upon infusion. PLs can be used to stabilize the injectable lipid emulsion by coating the submicron lipid droplets, thereby imparting an electrostatic charge on each and preventing coalescence.

For example, as mentioned, due to the high PL content of krill oil, and the propensity for excess phospholipids in relation to triglycerides in a given formulation that causes hypertriglyceridemia, there can be concentration limits to the fraction of krill oil that can be present in the oil phase of the parenteral emulsion using current krill oil compositions.[1] As a starting point, we know that the ideal PL:TG ratio is 0.06, so, for example, in a 20%$_{w/v}$ oil-in-water emulsion, 12 g of PL/1000 mL meets this ratio. If we assume that one type of krill oil contains approximately 30% PL, and that it has equivalent surfactant properties as conventional egg PLs, then the total krill oil content in a formulation can be adjusted accordingly as shown in Table 3. Thus, in this example, for every 1 g of krill oil, there is 0.3 g of PL present, so therefore up to 40 g can be included in an injectable emulsion, assuming that no additional PL, such as egg phospholipids, are added. For this to occur, the efficacy of krill oil as an equivalent surfactant (i.e., from a pharmaceutical and safety perspective) can be established against the standard parenteral surfactant, egg phospholipids (see below). In the present case, it is assumed that 40 g of krill oil provides equivalent surfactant properties as 12 g of egg phospholipids.

With this presumption, the following are possible formulations employing krill oil as part of a lipid injectable emulsion (International Application No. PCT/US2010/000723), as shown in Table 4 to illustrate some possibilities. If krill oil can be shown to exhibit equivalent behavior as a surfactant in the form of egg phospholipids, then it can replace the latter altogether, or alternatively, it may be used to supplement a portion of the conventional emulsifier. Again, as in the above example, a number of surfactant combinations are possible to optimize the stability of the emulsion system. Several additional examples are shown in Table 5 to exemplify this application using a 20% w/v oil-in-water emulsion (International Application No. PCT/US2010/000723), with 12 g/L of phospholipids using a higher PL-containing krill oil, but these examples are not meant in any way to be inclusive of the possible combinations, but merely to illustrate the concepts in this application. The efficacy of krill oil as a surfactant will be tested against egg phospholipids, since we know that it is a mixture of PLs that provide for the best surfactant. It can be recognized that purifying krill oil may remove trace, but important, amounts of surfactants which may alter surfactant activity much in the same way that purified egg lecithin, i.e., purified emulsifiers (phosphatidyl choline) have been shown to be inferior to non-purified lecithin. Also, purifying fish may also remove seemingly undesirable, but possibly essential, fatty acids found in small amounts. At present, reduced stability has been observed during stress testing of marine oil-containing injectable emulsions stabilized by egg phospholipids, compared to plant oil-containing injectable emulsions as depicted in Table 6. A marine oil-based PL-surfactant, such as krill oil, may improve the physical stability of very long-chain triglycerides such as the 20-carbon EPA and 22-carbon DHA, recognizing that the longer the hydrocarbon chain length, the greater the stress (i.e., interfacial tension) between the aqueous and oil phases of the emulsion, and consequently the greater the stress upon the surfactant to maintain physical stability.[9] Krill oil PLs may uniquely exhibit greater stability for these marine oil-based very long-chain triglycerides compared to conventional egg phospholipids emulsifiers when used for conventional 18-carbon long-chain triglycerides from plant sources such as soybean or olive oil. Thus, use of krill oil as a primary or co-surfactant in various high concentration fish oil-in-water parenteral emulsions may significantly improve the physical stability of these very long-chain triglyceride dispersions.

According to another exemplary aspect, a method of parenterally administering a composition is provided, the method comprising parenterally administering to a person a composition containing krill oil in a parenteral oil-in-water emulsion that contains protective concentrations of the naturally-occurring anti-oxidant, astaxanthin, against chemical breakdown or oxidation of the unsaturated n3-FAs present. As described earlier, oxidation of the polyunsaturated n3-FAs leads to the formation of reactive oxygen species that may be harmful upon intravenous administration. Thus, a specific omega-3 rich oil-in-water emulsion needs protection against chemical breakdown. Astaxanthin, found in krill oil, may provide unique protection against the oxidation of the omega-3 fatty acids similar to the presence of alpha-tocopherol in soybean oil that protects against oxidation of the omega-6 fatty acids. As such, just as marine-based PLs found in krill oil contain a high concentration of n3-FAs which may uniquely enhance the physical stability of the emulsion, so too may the presence of astaxanthin in krill oil uniquely enhance the chemical stability of the oil-in-water emulsion. Like the exemplary aspects of krill oil as a primary surfactant, or co-surfactant with egg phospholipids, it might be that astaxanthin can be the primary antioxidant, or co-antioxidant with alpha-tocopherol.

According to another exemplary aspect, a method of parenterally administering a composition is provided, the method comprising parenterally administering to a person a composition containing krill oil in a parenteral oil-in-water emulsion as a pharmaceutical drug vehicle to help solubilize highly lipophilic drugs in sufficient concentrations so as to be a therapeutically feasible injectable dosage form. Water-insoluble drugs, such as propofol, diazepam, and clevidipine, are but a few examples of current drugs that might benefit from krill oil containing high PL levels. What PL level is applied for a given formulation will vary with the drug, and may in fact be tailored to a specific drug or pro-drug, as the case may be.

According to another exemplary aspect, a method of parenterally administering a composition is provided, the method comprising parenterally administering to a person a composition containing krill oil in a parenteral oil-in-water emulsion as a pharmaceutical drug vehicle to help solubilize highly lipophilic drugs in sufficient concentrations in the oil phase, along with a water-soluble salt of said drug in the aqueous phase, so as to be a therapeutically feasible injectable dosage form. In this aspect, the drug may exist as a free acid or base, but may also be present in the same dosage form as a water-soluble salt. For example, the drug ketorolac is highly water insoluble as the free acid, but also exists as the water-soluble tromethamine salt and as such a commercial product currently exists in an aqueous injection at 30 mg/mL. The drug may be better tolerated (e.g., reduced risk of peripheral vein thrombophlebitis) if a portion of the drug is divided between the aqueous and nonaqueous phases of the emulsion. For example, in a conventional oil-in-water emulsion, the oil phase is the internal, or dispersed, phase, where the free acid would reside, and the external, or aqueous, phase would contain the corresponding water-soluble salt. How much it resides in each phase will depend upon the most desirable location with the least side effects. At present, there are cases where the lipophilic drug is intended to reside in the dispersed phase, but some free form of the drug in low concentrations is evitably present in the aqueous phase, where it has caused phlebitis. For example, propofol dispersed in a long-chain triglyceride (LCT) source, such as soybean oil-in-water emulsion has a higher phlebitis rate than a similar product, but where the lipid phase is now a 1:1 mixture of long-chain and medium-chain triglycerides (MCTs).[10] The improvement in phlebitis symptoms in the latter formulation appears to be related to a reduced aqueous concentration of free propofol, presumably due to enhanced incorporation of the free drug into both lipid fractions, while minimizing the concentration of propofol in the aqueous phase. Therefore, the exemplary aspect described herein is the unique and deliberate use of one or both phases of the emulsion to achieve the optimal dosage form that can safely and efficaciously deliver the active pharmaceutical ingredient (U.S. application Ser. No. 12/923,257).

According to another exemplary aspect, a method of parenterally administering a composition is provided, the method comprising parenterally administering to a person a composition containing krill oil in a parenteral oil-in-water emulsion as a therapeutic drug vehicle providing n3 fatty acids to mitigate adverse drug effects to vital organs (brain, heart, lungs, liver and kidney) involving inflammation, oxidative stress, immune modulation and/or ischemic events. The use of krill oil alone or in combination with fish oil triglycerides can be included in a parenteral dosage form for drugs known to cause damage to vital organs whose mechanism of injury involves inflammation, oxidative stress, ischemia and/or immune dysfunction as previously described in U.S. application Ser. No. 12/923,257.

According to another exemplary aspect, a method of parenterally administering a composition is provided, the method comprising parenterally administering to a person a composition containing krill oil in a parenteral oil-in-water emulsion as a safer treatment for endotoxicosis during severe sepsis. Endotoxin, and more specifically lipoploysaccharide (LPS), is present in the outermost membrane of bacterial cell walls, and is capable of eliciting a profound systemic inflammatory response in patients with blood stream infections. As the body responds to the presence of microorganisms in the blood stream via normal immune responses, e.g., phagocytosis, the bacterial cell wall is broken down and the Lipid A component of the outer cell wall remnant is released into the systemic circulation, where it stimulates the immune response and provokes systemic inflammation through various endogenous mediators involving cytokines, e.g., interleukin-1 (IL-1), tumor necrosis factor (TNF), eicosanoids (prostaglandins, thromboxanes, leukotrienes), catecholamines and hormones. In the infected patient, LPS can produce "systemic inflammatory response syndrome", or SIRS, that is characterized by dysregulations in body temperature, white blood cell counts, glucose homeostasis, coagulation, and vital organs functions (brain, heart, lungs, liver and kidneys). In a classical study of patient outcomes from SIRS, the mortality rate rose from 7% for non-infectious causes to as high as 46% from infectious causes.[11] Treatment for severe sepsis or septic shock has been directed at neutralizing the effects of endotoxin with antibodies or with agents that bind the endotoxin in the blood stream, rendering it inactive with lipoproteins or phospholipids. To date, these approaches have not been effective and have been associated with significant safety issues.

As described earlier, PLs have been shown to confer a significant survival advantage in animals, but they ultimately failed in clinical trials. The phospholipid agent used in these trials contained 92.5% soy phosphatidyl choline and 7.5% soy triglycerides.[6] As the PL concentrations in krill oil are present in amounts up to 60% w/w, with phosphatidyl choline as a major phosphatide constituent, krill oil may be an effective alternative to previous attempts in treating endotoxicosis using higher concentration PL formulations derived from vegetable sources. For example, approximately 50% of the fatty acid profile of soybean oil triglycerides consists of the pro-inflammatory omega-6 fatty acid (n6-FA) linoleic acid (18:2n6), which may adversely accentuate the inflammatory response during SIRS and sepsis. Moreover, intravenous fat emulsions stabilized by soy-based phosphatides have been associated with severely adverse effects in laboratory animals, whereas egg phospholipids were shown to be devoid of these effects.[12] Of six animals receiving these emulsions, 2 died within 48 hours of starting the infusion, and the remaining four developed "significant hyperpyrexia" following infusion, along with an approximate 50% reduction in food and water intake.[12] At present, egg phospholipids are nearly universally used in most nutritional and drug-containing injectable lipid emulsions. In contrast, given the unique composition of krill oil, which contains the less anti-inflammatory n3-FAs, contains a lower PL concentration, and can be stabilized with either egg PLs alone, krill oil PLs alone, or a combination of the two, the use of krill oil may avert previous clinical problems. These changes may yield a safer and more effective treatment option for endotoxin therapy in acutely ill patients with sepsis.

According to another exemplary aspect, a method of parenterally administering a composition is provided, the method comprising parenterally administering to a person a composition containing krill oil in a parenteral oil-in-water emulsion as an antidote to bind highly lipophilic drugs that may cause systemic toxicity.[13] Lipid emulsions have been used in the treatment of toxicity arising from lipophilic drugs, such as local anesthetics (e.g., bupivicaine), tricyclic antidepressants (e.g., amitryptyline) and cardiovascular agents including calcium channel blockers (e.g., verapamil) and antiarrhythmics (e.g., amiodarone), and in organophosphate poisoning from insecticides, etc. Presumably, the lipid emulsion vehicle sequesters the drug from the blood stream, thereby reducing the toxic manifestation caused by the free drug in the circulation. Unfortunately, there are limits to the delivery rate and volume of conventional long-chain triglyceride-based injectable emulsions that can be safely administered. Currently, a soybean oil-in-water emulsion is most widely used, but contains high amounts of pro-inflammatory n6-FAs (i.e., linoleic acid). When administered by rapid intravenous administration, they can produce acute, and clinically significant pulmonary gas diffusion abnormalities,[5] that would be particularly undesirable in the unconscious patient with drug overdose, especially in the absence of mechanical ventilation. Moreover, the maximum metabolic capacity of the human body to clear long-chain triglycerides is approximately 0.11 g/kg/hour,[5] and thus, complications to other vital organs (e.g., liver), as well as coagulation disorders from fat overload syndrome, can occur. In a test of the safety of high volume lipid infusion in laboratory animals, doses of 20% soybean oil-in-water emulsion ranging from 20 to 80 mL/kg were administered over 30 minutes, with lethal doses occurring at 60 and 80 mL/kg, but all doses were much higher than those used in the clinical setting as an antidote, of approximately 5 mL/kg.[14] Even at this lower human dose, current use of this injectable emulsions as antidote therapy clearly exceeds the metabolic capacity in humans in a 30 minute infusion (i.e., by >1 log higher). Use of a specially designed injectable emulsion containing only krill oil, or krill oil possibly in combination with a small amount of triglycerides, may be a safer and more effective antidote for lipophilic drug toxicities. This is because PLs are most likely responsible for binding and inactivating lipophilic drugs that cause toxicity, just as the same PLs are components for neutralizing the adverse sequelae of endotoxin. Hence, the safe, as well as effective delivery of PL infusions is most desirable and krill oil injectable emulsions may be uniquely beneficial in this regard.

According to another exemplary aspect, a method of parenterally administering a composition is provided, the method comprising parenterally administering to a person a composition containing krill oil in a parenteral oil-in-water emulsion as a source of n3-FAs to prevent essential fatty acid deficiency (EFAD). For example, to prevent EFAD in humans, at least 1% of the calories can come from the diet typically as linoleic acid (18:2n6), and approximately 0.5% from alpha-linolenic acid (18:3n3), in order to meet the n6- and n3-fatty acid (FA) requirements, respectively.[15] Thus, for example, in a 40 kg patient receiving a 1000 kcal diet, where soybean oil is the principal fat source (FA profile containing approximately 50% linoleic acid and approximately 10% alpha-linolenic acid), approximately 2 grams would meet n6-FA needs, whereas to meet n6-FA and n3-FA requirements, approximately 5 grams would have to be provided. But unlike common vegetable oil sources used in injectable lipid emulsions, marine oils (e.g., fish oil triglycerides and krill oil phospholipids) contain approximately 0.5% of the total FA profile as the essential n6-FA, arachidonic acid (AA), and approximately 20 to 60% as the essential n3-FAs, EPA and DHA. This is an important point since conventional vegetable oil sources do not contain appreciable amounts of these essential fatty acids (EFAs), but instead contain mainly their precursors that need to be metabolized enzymatically via several desaturation and elongation steps to form the 20- and 22-carbon EFAs from their 18-carbon sources. Thus, a much reduced quantity of the essential fatty acids is necessary, since the conversion to these bioactive end products is not 100% efficient, which is especially true for the formation of EPA and DHA from alpha-linolenic acid (18:3n3). Moreover, a recent review of the experience of Children's Hospital in Boston in treating over 90 infants with parenteral nutrition-related liver disease or PNALD, providing a 100% fish oil emulsion as monotherapy at 1 g/kg/day, has shown to be "safe and efficacious in reversing PNALD and normalizing EFAD status.[16] Of note, the fish oil injectable emulsion that was used contained between 0.1 to 0.4% AA (20:4n6), so it appears that, at least in the case of infants, a very small dose of krill oil could be used to prevent EFAD, and in amounts that do not interfere with the plasma clearance of infused triglycerides. More recently, the same group recently published its findings for a unique cohort of 10 children receiving parenteral nutrition with fish oil as the sole source of fat calories for a median duration of 14 weeks without evidence of EFAD.[17] It is possible that similarly low levels of AA would be sufficient in adults, but it has not yet been tested in this population. Thus, small amounts of krill oil in a parenteral emulsion formulation could prevent EFAD. Nonetheless, the krill oil composition could be modified to contain higher amounts of AA in tailoring the composition to this indication.

According to another exemplary aspect, a method of parenterally administering a composition is provided, the method comprising parenterally administering to a person a composition comprising krill oil in a parenteral oil-in-water emulsion as a daily caloric source of lipids in conjunction with other oils present as shown in Table 1. It is possible that krill oil can be added to current injectable oil-in-water emulsions as a daily caloric source. Due to the limitation that will be likely imposed because of its high PL content, current krill oil compositions[1] will not be a major fat source, but rather complimentary to other oils present when fat is used to meet caloric requirements. At present, there are a number of mixed-oil emulsions (e.g., soybean-MCT oils, soybean-olive oils, soybean-MCT-fish oils, soybean MCT-olive-fish oils), where krill oil might be added in small amounts as a means of achieving a unique modified oil mixture. Alternatively, chemical modifications of krill oil may allow greater utility as a daily caloric source.

According to another exemplary aspect, a method of parenterally administering a composition is provided, the method comprising parenterally administering to a person a composition containing krill oil in a parenteral oil-in-water emulsion as a specific source of omega-3 or n3 fatty acids, EPA and DHA. In some patients, for example, those requiring long-term parenteral nutrition support, the chronic provision of a modest amount of EPA and DHA in existing nutrition support regimens could favorably influence the otherwise inevitable development of end-stage liver disease over long periods of time. Alternatively, chemical modifications of krill oil may allow greater utility as a source of n3-FAs.

According to another exemplary aspect, a method of parenterally administering a composition is provided, the method comprising parenterally administering to a person a composition comprising krill oil in a parenteral oil-in-water emulsion as a source of n3-FAs to meet essential fatty acids requirements, and/or a daily caloric source of lipids in conjunction with other oils present, and/or a specific source of omega-3 or n3 fatty acids, EPA and DHA, and/or as an alternative surfactant to egg lecithin or in combination with egg lecithin to improve the physical stability of the emulsion. Alternatively, chemical modifications of krill oil may allow greater utility to meet these multiple uses.

According to another exemplary aspect, a method of parenterally administering a composition is provided, the method comprising parenterally administering to a person a composition comprising krill oil in a parenteral oil-in-water emulsion as an alternative and economically viable source of n3-FAs instead of conventional fish-derived sources. That is, as fish populations decline, krill populations will remain plentiful, and therefore they could become the principal source of omega-3 fatty acids, and thereby allow fish stocks to be replenished accordingly. Thus, purification and chemical separation of the n3-FAs and re-esterification to, for examples, ethyl esters, phospholipids and/or triglyceride molecules would be possible from a single marine oil source for multiple dosage forms.

TABLE 1

20% Oil-in-Water Krill Oil-Containing Emulsion Examples

| *PHARMACEUTICAL INGREDIENT | SAMPLE CONCENTRATION | RANGE OF CONCENTRATIONS |
|---|---|---|
| Krill Oil | 40 g/L | 12 to 200 g/L |
| Total Phospholipids | 45% w/w | 20 to 60% w/w |
| Total Triglycerides | 30% w/w | 15 to 45% w/w |
| Sum of n3-FA | 35% w/w | 20 to 60% w/w |
| EPA (20:5n3) | 9 g/L | 1.6 to 80 g/L |
| DHA (22:6n3) | 5 g/L | 0.8 to 40 g/L |
| AA (20:4n6) | 0.2 g/L | 0.06 to 1.0 g/L |
| astaxanthin | 0.04 g/L | 0.012 to 0.2 g/L |
| Fish Oil | 100 g/L | 0 to 180 g/L |
| Sum of n3-FA | 45% w/w | ≥45% w/w |
| EPA (20:5n3) | 30 g/L | 0 to 54 g/L |
| DHA (22:6n3) | 15 g/L | 0 to 27 g/L |
| AA (20:4n6) | 0.5 g/L | 0 to 0.9 g/L |
| Total n3-FA | 59 g/L | 2.4 to 120 g/L |
| Total n6-FA | 0.7 g/L | 0.06 to 1.0 g/L |
| MCT Oil | 60 g/L | 0 to 100 g/L |
| Approved Pharmaceutical Excipients | | |
| Glycerol | 22.5 g/L | 20 to 25 g/L |
| Egg Phospholipids | 0 g/L | 0 to 18 g/L |
| Sodium Oleate | 2.5 g/L | 0 to 5 g/L |
| α-tocopherol | 0.2 g/L | 0 to 1 g/L |
| Sterile Water for Inj. | q.s. ad 1000.0 | Fixed |

TABLE 2

Examples of Modified Krill Oil Compositions, % w/w

| EPA[1] | DHA[2] | Total n3FA[3] | Total PL[4] | PL-n3FA[5] | Total TG[6] | TG-n3FA[7] |
|---|---|---|---|---|---|---|
| 30 | 15 | 45 | 10 | 20 | 70 | 80 |
| 30 | 15 | 45 | 20 | 30 | 60 | 70 |
| 30 | 15 | 45 | 30 | 40 | 50 | 60 |
| 30 | 15 | 45 | 40 | 50 | 40 | 50 |
| 30 | 15 | 45 | 50 | 60 | 30 | 40 |
| 30 | 15 | 45 | 60 | 70 | 20 | 30 |
| 30 | 15 | 45 | 70 | 80 | 10 | 20 |
| 40 | 20 | 60 | 10 | 20 | 70 | 80 |
| 40 | 20 | 60 | 20 | 30 | 60 | 70 |
| 40 | 20 | 60 | 30 | 40 | 50 | 60 |
| 40 | 20 | 60 | 40 | 50 | 40 | 50 |
| 40 | 20 | 60 | 50 | 60 | 30 | 40 |
| 40 | 20 | 60 | 60 | 70 | 20 | 30 |
| 40 | 20 | 60 | 70 | 80 | 10 | 20 |
| 15 | 30 | 45 | 10 | 20 | 70 | 80 |
| 15 | 30 | 45 | 20 | 30 | 60 | 70 |
| 15 | 30 | 45 | 30 | 40 | 50 | 60 |
| 15 | 30 | 45 | 40 | 50 | 40 | 50 |
| 15 | 30 | 45 | 50 | 60 | 30 | 40 |
| 15 | 30 | 45 | 60 | 70 | 20 | 30 |
| 15 | 30 | 45 | 70 | 80 | 10 | 20 |
| 20 | 40 | 60 | 10 | 20 | 70 | 80 |
| 20 | 40 | 60 | 20 | 30 | 60 | 70 |
| 20 | 40 | 60 | 30 | 40 | 50 | 60 |
| 20 | 40 | 60 | 40 | 50 | 40 | 50 |
| 20 | 40 | 60 | 50 | 60 | 30 | 40 |
| 20 | 40 | 60 | 60 | 70 | 20 | 30 |
| 20 | 40 | 60 | 70 | 80 | 10 | 20 |

[1] EPA = eicosapentaenoic acid (20:5n3)
[2] DHA = docosapentaenoic acid (22:6n3)
[3] Total n3FA = total omega-3 or n3 fatty acids
[4] Total PL = total phospholipids
[5] PL-n3FA = amount of omega-3 fatty acids in phospholipids
[6] Total TG = total triglycerides
[7] TG-n3FA = amount of omega-3 fatty acids in triglycerides

TABLE 3

Examples of Krill oil as a Surfactant or Co-Surfactant, 30% PL

| Krill Oil (g) | Egg Phospholipids (g) |
|---|---|
| 0 | 12.0 |
| 1 | 11.7 |
| 2 | 11.4 |
| 3 | 11.1 |
| 4 | 10.8 |
| 5 | 10.5 |
| 6 | 10.2 |
| 7 | 9.9 |
| 8 | 9.6 |
| 9 | 9.3 |
| 10 | 9.0 |
| 11 | 8.7 |
| 12 | 8.4 |
| 13 | 8.1 |
| 14 | 7.8 |
| 15 | 7.5 |
| 16 | 7.2 |
| 17 | 6.9 |
| 18 | 6.6 |
| 19 | 6.3 |
| 20 | 6.0 |
| 21 | 5.7 |
| 22 | 5.4 |
| 23 | 5.1 |
| 24 | 4.8 |
| 25 | 4.5 |
| 26 | 4.2 |
| 27 | 3.9 |
| 28 | 3.6 |

TABLE 3-continued

Examples of Krill oil as a Surfactant or Co-Surfactant, 30% PL

| Krill Oil (g) | Egg Phospholipids (g) |
|---|---|
| 29 | 3.3 |
| 30 | 3.0 |
| 31 | 2.7 |
| 32 | 2.4 |
| 33 | 2.1 |
| 34 | 1.8 |
| 35 | 1.5 |
| 36 | 1.2 |
| 37 | 0.9 |
| 38 | 0.6 |
| 39 | 0.3 |
| 40 | 0 |

TABLE 4

Examples of Krill Oil (30% PL) as an Oil-in-Water Emulsion

| Krill Oil* | | Fish Oil** | | MCT | Egg | Total |
|---|---|---|---|---|---|---|
| g/L | n3-FAs, g/L | g/L | n3-FAs, g/L | Oil g/L | Phospholipids g/L | n3-FA, g g/L |
| | Assumes LipOmega-3 MCT 90/10 (marine oil = fish oil plus krill oil by weight) | | | | | |
| 40 | 8.0 | 180 | 81.0 | 20 | 0 | 89.0 |
| 30 | 6.0 | 180 | 81.0 | 20 | 3 | 87.0 |
| 20 | 4.0 | 180 | 81.0 | 20 | 6 | 85.0 |
| 10 | 2.0 | 180 | 81.0 | 20 | 9 | 83.0 |
| | Assumes LipOmega-3 MCT 90/10 (marine oil = fish oil minus krill oil by weight) | | | | | |
| 40 | 8.0 | 140 | 63.0 | 16 | 0 | 71.0 |
| 30 | 6.0 | 150 | 67.5 | 16.5 | 3 | 73.5 |
| 20 | 4.0 | 160 | 72.0 | 17 | 6 | 76.0 |
| 10 | 2.0 | 170 | 76.5 | 19 | 9 | 78.5 |
| | Assumes LipOmega-3 MCT 50/50 (marine oil = fish oil plus krill oil by weight) | | | | | |
| 40 | 8.0 | 100 | 45.0 | 100 | 0 | 53.0 |
| 30 | 6.0 | 100 | 45.0 | 100 | 3 | 51.0 |
| 20 | 4.0 | 100 | 45.0 | 100 | 6 | 49.0 |
| 10 | 2.0 | 100 | 45.0 | 100 | 9 | 47.0 |
| | Assumes LipOmega-3 MCT 50/50 (marine oil = fish oil minus krill oil by weight) | | | | | |
| 40 | 8.0 | 80 | 36.0 | 80 | 0 | 44.0 |
| 30 | 6.0 | 85 | 38.3 | 85 | 3 | 44.3 |
| 20 | 4.0 | 90 | 40.5 | 90 | 6 | 44.5 |
| 10 | 2.0 | 95 | 42.8 | 95 | 9 | 44.8 |

*Assumes: Krill Oil = 30% PL (12 g/L of egg PL = 40 g/L krill PL), minimum EPA + DHA = 20%;
**Fish Oil: meets requirements of Pharm Eur Monograph 1352, minimum EPA + DHA = 45%

TABLE 5

Examples of Krill Oil (50% PL) as an Oil-in-Water Emulsion

| Krill Oil* | | Fish Oil** | | MCT | Egg | Total |
|---|---|---|---|---|---|---|
| g/L | n3-FAs, g/L | g/L | n3-FAs, g/L | Oil g/L | Phospholipids g/L | n3-FA, g g/L |
| | Assumes LipOmega-3 MCT 90/10 (marine oil = fish oil plus krill oil by weight) | | | | | |
| 24 | 4.8 | 180 | 81.0 | 20 | 0 | 85.8 |
| 18 | 3.6 | 180 | 81.0 | 20 | 3 | 84.6 |
| 12 | 2.4 | 180 | 81.0 | 20 | 6 | 83.4 |
| 6 | 1.2 | 180 | 81.0 | 20 | 9 | 82.2 |
| | Assumes LipOmega-3 MCT 90/10 (marine oil = fish oil minus krill oil by weight) | | | | | |
| 24 | 4.8 | 156 | 70.2 | 16 | 0 | 75.0 |
| 18 | 3.6 | 162 | 72.9 | 16.5 | 3 | 76.5 |
| 12 | 2.4 | 168 | 75.6 | 17 | 6 | 78.0 |
| 6 | 1.2 | 174 | 78.3 | 19 | 9 | 79.5 |
| | Assumes LipOmega-3 MCT 50/50 (marine oil = fish oil plus krill oil by weight) | | | | | |
| 24 | 4.8 | 100 | 45.0 | 100 | 0 | 49.8 |
| 18 | 3.6 | 100 | 45.0 | 100 | 3 | 48.6 |
| 12 | 2.4 | 100 | 45.0 | 100 | 6 | 47.4 |
| 6 | 1.2 | 100 | 45.0 | 100 | 9 | 46.2 |
| | Assumes LipOmega-3 MCT 50/50 (marine oil = fish oil minus krill oil by weight) | | | | | |
| 24 | 4.8 | 76 | 34.2 | 80 | 0 | 39.0 |
| 18 | 3.6 | 82 | 36.9 | 85 | 3 | 40.5 |
| 12 | 2.4 | 88 | 39.6 | 90 | 6 | 42.0 |
| 6 | 1.2 | 94 | 42.3 | 95 | 9 | 43.5 |

*Assumes: Krill Oil = 50% PL (12 g/L of egg PL = 24 g/L krill PL), minimum EPA + DHA = 20%;
**Fish Oil: meets requirements of Pharm Eur Monograph 1352, minimum EPA + DHA = 45%

TABLE 6

Stability of Lipid Injectable Emulsions of Varying Oil Composition Under Stress Conditions
Stress Conditions for Lipid Injectable Emulsions

| | Oil(s) | | | | | | |
|---|---|---|---|---|---|---|---|
| | 20% oil-in-water emulsion | | | | 5% oil-in-water emulsion | | |
| Oil(s) | Total Samples | PFAT5 > 0.5% | Peak PFAT5 | % Fail | Total Samples | PFAT5 > 0.5% | Peak PFAT5 | % Fail |
| Plant Oil-1 | | | | | | | | |
| Stress-1* | 32 | 0 | 0.043 | 0 | 32 | 0 | 0.050 | 0 |
| Stress-2* | 32 | 0 | 0.044 | 0 | 32 | 1 | 0.055 | 3.13 |
| Stress-3* | 32 | 0 | 0.043 | 0 | 32 | 1 | 0.055 | 3.13 |
| Stress-4* | 32 | 0 | 0.046 | 0 | 32 | 0 | 0.043 | 0 |

TABLE 6-continued

Stability of Lipid Injectable Emulsions of Varying Oil Composition
Under Stress Conditions
Stress Conditions for Lipid Injectable Emulsions

| | Oil(s) | | | | | | | |
|---|---|---|---|---|---|---|---|---|
| | 20% oil-in-water emulsion | | | | 5% oil-in-water emulsion | | | |
| Oil(s) | Total Samples | PFAT5 > 0.5% | Peak PFAT5 | % Fail | Total Samples | PFAT5 > 0.5% | Peak PFAT5 | % Fail |
| Plant Oil-2 | | | | | | | | |
| Stress-1 | 48 | 0 | 0.029 | 0 | 48 | 0 | 0.033 | 0 |
| Stress-2 | 48 | 0 | 0.033 | 0 | 48 | 2 | 0.057 | 4.17 |
| Stress-3 | 48 | 0 | 0.046 | 0 | 48 | 1 | 0.058 | 2.06 |
| Stress-4 | 48 | 0 | 0.031 | 0 | 48 | 0 | 0.048 | 0 |
| Marine Oil | | | | | | | | |
| Stress-1 | 48 | 0 | 0.026 | 0 | 48 | 0 | 0.028 | 0 |
| Stress-2 | 48 | 5 | 0.071 | 10.42 | 48 | 10 | 0.106 | 20.83 |
| Stress-3 | 48 | 0 | 0.038 | 0 | 48 | 9 | 0.091 | 18.75 |
| Stress-4 | 48 | 5 | 0.065 | 10.42 | 48 | 9 | 0.099 | 18.75 |

*Applied as per: U.S. Pat. No. 7,150,996 (Dec. 19, 2006)

REFERENCES

1. Bruheim I et al. Bioeffective krill oil compositions. U.S. Patent Application Publication No. 2008/0274203, Nov. 6, 2008.
2. Omega-3 Säuren-Triglyceride, 2005. Monograph 1352, German Pharmacopeia, Kommentar zur Ph. Eur. 5.0, 22 Lfg., pp. 1-4
3. Driscoll D F, Ling P R, Bistrian B R. Pharmacopeial compliance of fish oil-containing parenteral lipid emulsion mixtures: Globule size distribution (GSD) and fatty acid analyses. Int J. Pharm. 2009; 379(1):125-30
4. Winther B, Hoem N, Berge K, Reubsaet L. Elucidation of phosphatidylcholine composition in krill oil extracted from Euphausia superba. Lipids 2010; 45:25-36
5. Driscoll D F, Adolph M, Bistrian B R. Lipid emulsions in parenteral nutrition. In Parenteral Nutrition. Rombeau J. L., Rolandelli R. (eds): W. B. Saunders Company, Philadelphia, Pa., 2001, pp. 35-59
6. Gordon B R, Parker T S, Levine D M et al. Neutralization of endotoxin by phospholipids emulsion in healthy volunteers. J Infect Dis 2005; 191:1515-1522
7. Dellenger P, Tomayko J F, Angus D C et al. Efficacy and safety of a phospholipids emulsion (GR270773) in gram-negative severe sepsis: Results of a phase II multicenter, randomized, placebo-controlled, dose-finding clinical trial. Crit Care Med 2009; 37:29-38
8. Lee J S, Pinnamaneni S K, Eo S J et al. Saturated, but not n-6 polyunsaturated, fatty acids induce insulin resistance: role of intramuscular accumulation of lipid metabolites. J Appl Phsyiol 2006; 100:1467-74
9. Driscoll D F, Nehne J, Peterss H et al. The influence of medium-chain triglycerides on the stability of all-in-one formulations. Int J Pharm 2002; 240:1-10
10. Larsen B, Beerhalter U, Biedler A et al. Less pain on injection by a new formulation of propofol? A comparison with propofol LCT. Anaesthesist 2001; 50:842-45
11. Rangel-Fausto M S, Pittet D, Costigan M et al. The natural history of systemic inflammatory response syndrome (SIRS): A prospective study. JAMA 1995; 273:117-23
12. Jones L D, Castleberry M W, Canham J E, King N W. Toxicity testing of fat emulsions for intravenous administration. Am J Clin Nutr 1965; 16:62-67
13. Turner-Lawrence D E, Kerns W. Intravenous fat emulsion: a potential novel antidote. J Med Toxicol 2008; 4:109-14
14. Hiller D B, DiGregorio G, Kelly K et al. Safety of high volume lipid emulsion infusion. Reg Anesth Pain Med 2010; 35:140-44
15. Bistrian B R. Clinical aspects of essential fatty acid metabolism: Jonathan Rhoads Lecture. J Parenter Enter Nutr 2003; 27:168-75
16. de Meijer V E, Gura K M, Le H D et al. Fish oil-based lipid emulsions prevent and reverse parenteral nutrition-associated liver disease: The Boston experience. J Parenter Enter Nutr 2009; 33:541-47.
17. Le H D, deMeijer V E, Zurakowski D et al. Parenteral fish oil as monotherapy improves lipid profiles in children with parenteral nutrition-associated liver disease. J Parenter Enter Nutr 2010; 34:477-8

The invention claimed is:

1. A method of parenterally administering a composition, the method comprising parenterally administering to a person a composition comprising krill oil in an oil-in-water emulsion comprising:
   an n3-FA-containing phospholipid obtained from krill oil, and
   a fish oil containing an n3-FA-containing triglyceride,
   wherein the composition further comprises at least one drug, and wherein a portion of the at least one drug is present in the oil phase of the emulsion and a portion of the same at least one drug in a water-soluble salt is present in the aqueous phase of the emulsion.

2. The method according to claim 1, wherein the krill oil is present in an amount effective to increase the physical stability of the emulsion, in comparison with the physical stability of an identical emulsion containing egg lecithin in place of the krill oil.

3. The method according to claim 1, wherein the krill oil is present in an amount effective to increase the chemical stability of the emulsion, in comparison with the chemical stability of an identical emulsion containing alpha-tocopherol in place of the krill oil.

4. The method according to claim 1, wherein the composition comprises a highly lipophilic drug, and the krill oil is present in an amount effective to solubilize the highly lipophilic drug.

5. The method according to claim 1, wherein the composition comprises n3 fatty acids in an amount effective to mitigate adverse drug effects to vital organs involving inflammation, oxidative stress, immune modulation and/or ischemic events.

6. The method according to claim 1, wherein the method is a method for treating endotoxicosis during severe sepsis.

7. The method according to claim 1, wherein the method is a method for treating a person having toxic blood levels of highly lipophilic drugs.

8. The method according to claim 1, wherein the composition is substantially free of egg lecithin.

9. The method according to claim 1, wherein the krill oil contains EPA and DHA.

10. The method according to claim 1, wherein the composition is substantially free of n3-FAs from a fish-derived source.

11. The method according to claim 1, wherein the total phospholipid content is 10 to 70%$_{w/w}$, wherein 20 to 80% of the total n3-FA content is present in the phospholipid, wherein the total triglyceride content is from 10 to 70%$_{w/w}$, wherein 20 to 80% of the total n3-FA content is present in the triglyceride, and wherein the total n3-FA content is from 45 to 60%$_{w/w}$.

12. A parenterally applicable pharmaceutical composition, comprising an oil-in-water emulsion comprising:
   an n3-FA-containing phospholipid obtained from krill oil, and
   a fish oil containing an n3-FA-containing triglyceride,
   wherein the composition further comprises at least one drug, and wherein a portion of the at least one drug is present in the oil phase of the emulsion and a portion of the same at least one drug in a water-soluble salt is present in the aqueous phase of the emulsion.

13. The composition of claim 12, wherein the phospholipid obtained from krill oil is present in an amount effective to solubilize the drug.

14. The composition of claim 12, wherein the composition is suitable for use in the treatment of endotoxicosis during sepsis.

15. The composition of claim 12, wherein the composition is suitable for mitigating adverse drug effects to vital organs involving inflammation, oxidative stress, immune modulation and/or ischemic events.

16. The composition of claim 12, wherein the composition is suitable for use in the treatment of a person having toxic blood levels of highly lipophilic drugs.

17. The composition of claim 12, wherein the fish oil containing an n3-FA-containing triglyceride is present in an amount of about 5% to about 18% based on the weight of the composition.

18. The composition of claim 17, wherein in the fish oil containing an n3-FA-containing triglyceride, a sum of EPA and DHA expressed as triglycerides is at least 45%, and a total n3-FA expressed as triglycerides is at least 60%.

19. The composition of claim 12, further comprising a medium-chain triglyceride oil.

20. The composition of claim 12, wherein the composition does not contain a vegetable oil.

21. The composition of claim 12, wherein the krill oil is present in an amount effective to increase the physical stability of the emulsion, in comparison with the physical stability of an identical emulsion containing egg lecithin in place of the krill oil.

22. The composition of claim 12, wherein the krill oil is present in an amount effective to increase the chemical stability of the emulsion, in comparison with the chemical stability of an identical emulsion containing alpha-tocopherol in place of the krill oil.

23. A parenterally applicable pharmaceutical composition, consisting essentially of krill oil and fish oil in an oil-in-water emulsion,
   wherein the krill oil contains an n3-FA-containing phospholipid,
   wherein the fish oil containing an n3-FA-containing triglyceride, and
   wherein the composition further consists essentially of at least one drug, and wherein a portion of the at least one drug is present in the oil phase of the emulsion and a portion of the same at least one drug in a water-soluble salt is present in the aqueous phase of the emulsion.

24. The composition of claim 23, wherein the krill oil contains omega-3 fatty acid-containing phospholipids in an amount of about 20 to about 60%, based on the weight of the krill oil.

25. The composition of claim 24, wherein the omega-3 fatty acid-containing phospholipids contain DHA in an amount of about 10 to about 20%, based on the total fatty acid content of the phospholipids.

26. The composition of claim 23, wherein the krill oil contains omega-3 fatty acid-containing triglycerides in an amount of less than about 30%, based on the weight of the krill oil.

27. The composition of claim 24, wherein the omega-3 fatty acid-containing phospholipids contain EPA in an amount of about 20 to about 40%, based on the total fatty acid content of the phospholipids.

28. The composition of claim 23, wherein the krill oil is present in an amount of from about 1% to about 20%, based on the total weight of the composition.

29. The composition of claim 23, wherein the weight ratio of oil to water in the oil-and-water emulsion is from about 1:99 to about 20:80.

30. The composition of claim 23, wherein the fish oil containing an n3-FA-containing triglyceride is present in an amount of about 5% to about 18% based on the weight of the composition.

31. The composition of claim 30, wherein in the fish oil containing an n3-FA-containing triglyceride, a sum of EPA and DHA expressed as triglycerides is at least 45%, and a total n3-FA expressed as triglycerides is at least 60%.

32. The composition of claim 23, further comprising a medium-chain triglyceride.

33. The composition of claim 23, wherein the composition does not contain a vegetable oil.

34. A parenterally applicable pharmaceutical composition, comprising krill oil in an oil-in-water emulsion, wherein the krill oil contains an n3-FA-containing phospholipid, wherein the composition does not contain a vegetable oil,
   wherein the composition further comprises at least one drug, and wherein a portion of the at least one drug is present in the oil phase of the emulsion and a portion of the same at least one drug in a water-soluble salt is present in the aqueous phase of the emulsion.

35. The composition of claim 34, further comprising a fish oil containing an n3-FA-containing triglyceride, wherein the fish oil containing an n3-FA-containing triglyceride is present in an amount of about 5% to about 18% based on the weight of the composition.

* * * * *